United States Patent
Wilson

(10) Patent No.: US 7,354,504 B2
(45) Date of Patent: Apr. 8, 2008

(54) DIELECTRIC PROFILE CONTROLLED MICROWAVE STERILIZATION SYSTEM

(75) Inventor: David R. Wilson, Platteville, CO (US)

(73) Assignee: Frontier Engineering LLC, Platteville, CO (US)

( * ) Notice: Subject to any disclaimer, the term of this patent is extended or adjusted under 35 U.S.C. 154(b) by 176 days.

(21) Appl. No.: 11/437,399

(22) Filed: May 18, 2006

(65) Prior Publication Data

US 2007/0039949 A1    Feb. 22, 2007

Related U.S. Application Data

(60) Provisional application No. 60/682,497, filed on May 18, 2005.

(51) Int. Cl.
*A61L 2/12* (2006.01)
*A61L 12/06* (2006.01)
*H05B 6/64* (2006.01)
*C23C 16/511* (2006.01)

(52) U.S. Cl. .................. 204/157.43; 204/298.38; 219/678; 118/723 MW; 250/250; 250/492.1; 250/493.1

(58) Field of Classification Search .................. None
See application file for complete search history.

(56) References Cited

U.S. PATENT DOCUMENTS 6,045,671 A * 4/2000 Wu et al. ................ 506/40

OTHER PUBLICATIONS

U.S. Appl. No. 60/682,497, filed May 18, 2005, Wilson.

* cited by examiner

*Primary Examiner*—Nikita Wells
(74) *Attorney, Agent, or Firm*—Craig Miles; CR Miles, P.C.

(57) ABSTRACT

A dielectric profiler establishes a dielectric profile of microwave characteristics for identifying, sterilizing or inactivating a target material prior to performing a microwave irradiation event to sterilize or inactivate the target material.

20 Claims, 3 Drawing Sheets

US 7,354,504 B2

DIELECTRIC PROFILE CONTROLLED MICROWAVE STERILIZATION SYSTEM

Figure 1:
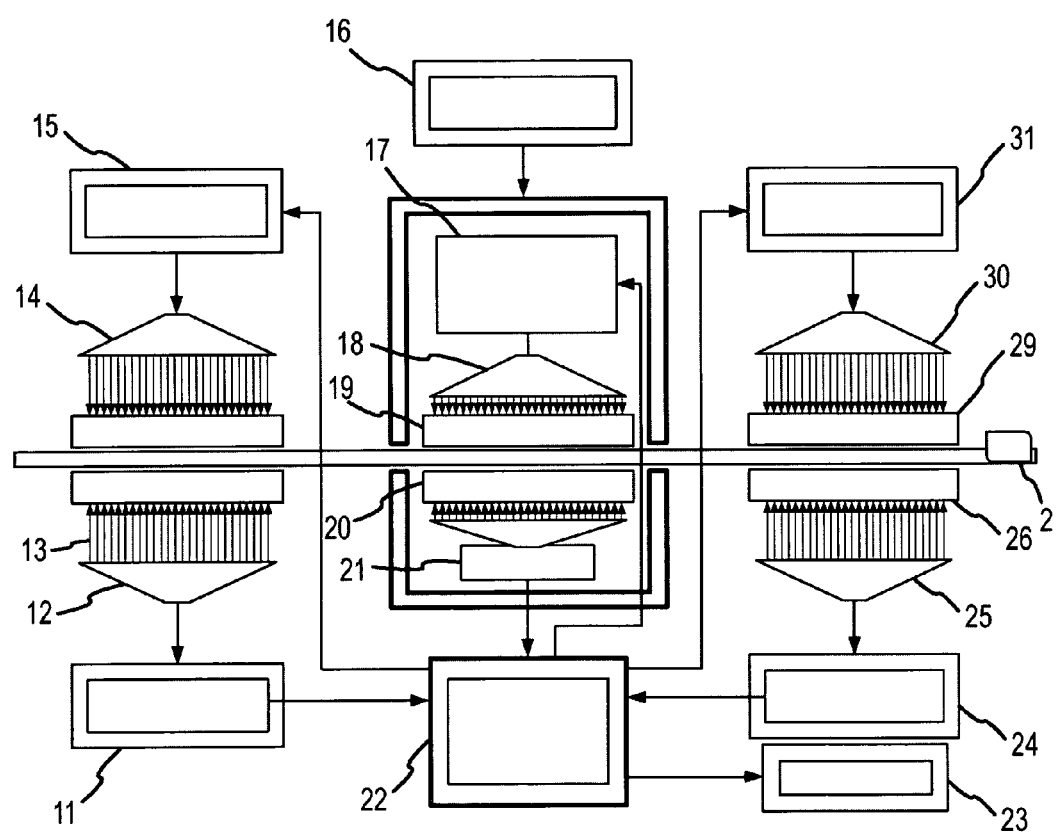

This United States Non-provisional Patent Application claims the benefit of U.S. Provisional Patent Application No. 60/682,497, filed May 18, 2005, hereby incorporated by reference herein.

I. BACKGROUND

Microwave radiation has been used to heat a wide variety of materials to the point where temperatures are sufficient to create sterilization effects. Many materials, especially those which have not absorbed moisture, may require prolonged exposure at high power levels to ensure complete sterilization.

However, the determination of when a material is rendered inactive or destroyed by irradiation with microwaves still relies largely upon observable changes of the irradiated material. This reliance upon observation of the irradiated material may be impractical when the irradiated material is divided among a large number of discrete containers or when the irradiated material is a biological pathogen or toxic chemical, or may be unlawful for example in the case of opening the United States mail to obtain samples of the irradiated material.

Moreover, conventional irradiation devices and irradiation methods suffer from a lack of precision. Conventional material irradiation devices and methods rely upon a fixed frequency microwave source which provides a high intensity, non-specific radiation field that may be many times stronger than is required to sterilize or heat a particular material because determination as to when a material has been rendered inactive remains largely a matter of guesswork in many cases.

As to these problems and other problems related with conventional microwave irradiation of materials for the purpose of sterilization or heating of a material, rendering the material inactive or destroying the material, the instant invention addresses each in practical fashion.

II. SUMMARY OF THE INVENTION

Accordingly, a broad object of the invention can be to provide a dielectric profiler which analyzes the dialect profile of a material over a wide frequency range which allows adjustment of the microwave frequency prior to material irradiation to achieve sterilization or heating.

Another broad object of the invention can be to provide a computer which operates a dielectric profiler application program which compensates for a numerous and wide variety of material variables including without limitation moisture, volume, temperature, density, contaminants, or the like, by use of calibration profiles retrievable from a computer memory element.

Another broad object of the invention can be to operate a dielectric profiler at power levels which avoid or reduce alteration of the target material (the "profiling event") prior to irradiation for the purpose of sterilization or heating. Many substances display an altered irradiation absorption profile once they have been exposed to any intense radio frequency field. In certain instances, the amount of microwave energy a material can absorb can be altered by increasing wavelength frequency of microwave irradiation. As such, application of a strong irradiation field at one frequency can alter material characteristics and hinder measurement of the dielectric characteristics of the material at a different frequency.

Another broad object of the invention can be to provide a method of microwave irradiation of a material which includes at least a first step of assessing the dielectric profile of a material to determine a frequency (or frequencies) at which to irradiate the material, and can include additional steps of assessing rate of change in temperature of the material at such established frequency (or frequencies) to establish a duration of an irradiation period at such frequency (or frequencies), irradiation of the material at such frequency (or frequencies) for such irradiation period (the "irradiation event"), comparison of the dielectric profile of the material before the irradiation event and the dielectric profile after the irradiation event, assessment based upon such comparison as to the degree to which the material has been altered by the irradiation event, and assessment based upon such comparison as to whether any undesired products have been generated by the irradiation event.

Another broad object of the invention can be to provide automatic detection and selective destruction or inactivation of a first material on the surface of a second material such as a manufacturing material; or of a first material contained inside a space defined by the configuration of a second material such as parcels, envelopes, boxes, containers, or the like; or of a first material such as mold or other pathogen located in the wall space of a building. However, these specific examples are not intended to be limiting with respect to the numerous and wide variety of applications encompassed by the invention.

Another broad object of the invention can be to provide for detection and identification of concealed materials such as bacteria, viruses, pathogens, cells, cell components, chemicals, compositions, or mixtures or combinations thereof, which as to certain embodiments of the invention, can further comprise the generation of 3D images of a concealed materials.

Naturally, further objects of the invention can be understood from the description and drawings.

III. A BRIEF DESCRIPTION OF THE DRAWINGS

FIG. 1 shows an embodiment of the invention which operates to provide both a profiling event and a microwave irradiation event of a target material.

Figure 2:
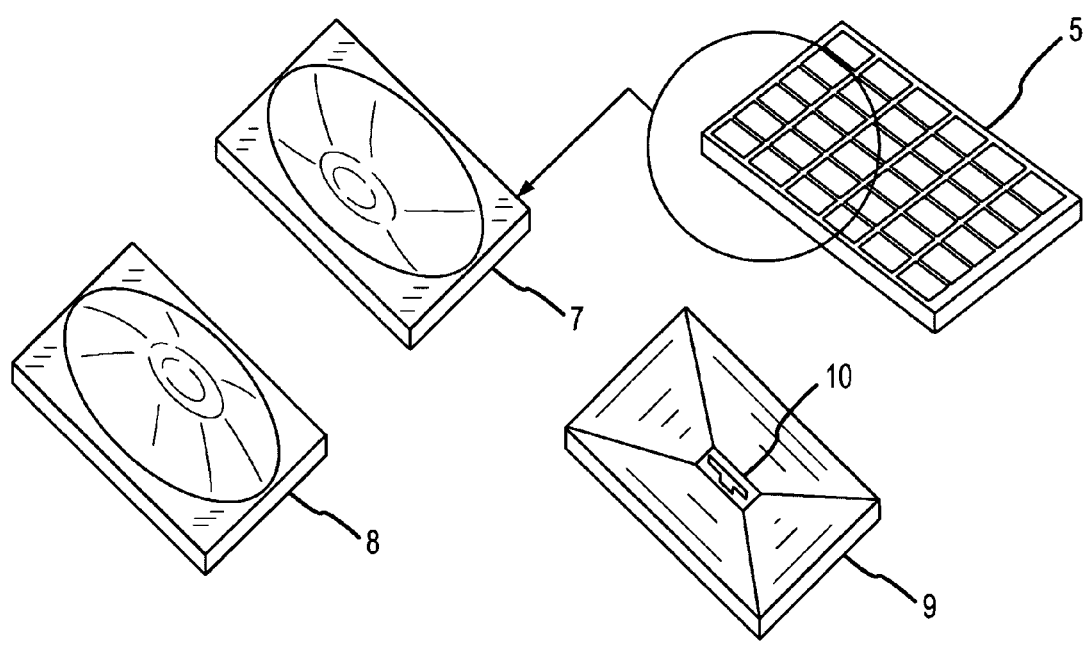

FIG. 2 provides non-limiting examples of configurations of microwave cells and arrays of microwave cells which can be used in embodiments of the invention to provide a profiling event or a microwave irradiation event of a target material.

Figure 3:
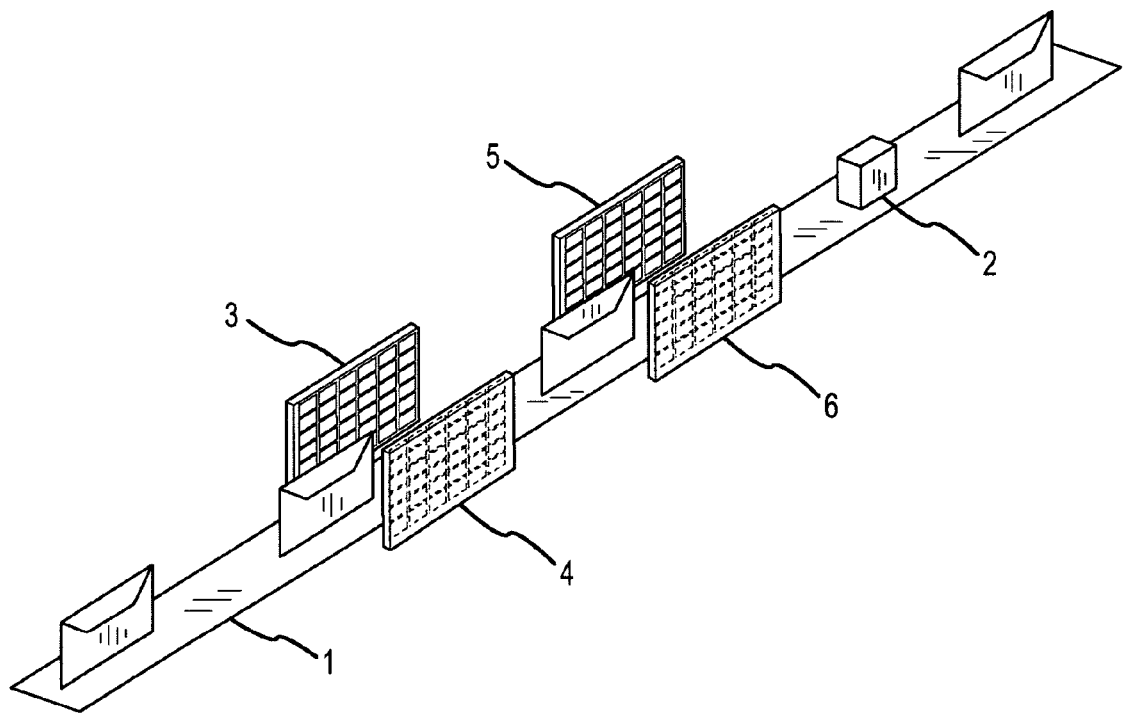

FIG. 3 shows a particular embodiment of the invention used to provide a profiling event or an irradiation event, or both, of a target material such as a letter or package.

IV. DETAILED DESCRIPTION OF THE PREFERRED EMBODIMENTS

A device and method of using microwaves to irradiate target material(s) which allows pre-selection of microwave characteristics to limit duration of the irradiation event, assess alteration of the material due to the irradiation event, and to detect undesired products generated by the irradiation event.

The term "target material" is intended to broadly encompass any manner of composition regardless of form or configuration which absorbs microwave radiation and with limitation animal tissue, plant tissue, biological particles such as bacteria, viruses, cells, cancer cells, tumors, inorganic materials which in certain cases may be rare, exotic, or precious materials such as gold, diamonds, or like or because the material is obtainable only in small quantity.

The term "microwave characteristic" is intended to broadly encompass any microwave frequency or combination of microwave frequencies, the power or power profile of such microwave frequency or combination of frequencies, the period or the periods in which microwave irradiation occurs whether continuous or discontinuous, or the like.

The term "sterilization" is intended to broadly encompass any alteration of the target material including without limitation killing or inactivating bacteria, viruses, pathogens molds, cells or components thereof; or inactivating or altering chemicals, toxins or the like; or increasing the temperature of a target material to a desired temperature.

Now referring primarily to FIG. 1, embodiments of the invention can generate a profile of the microwave characteristics of a target material(s) of interest. The profile of the microwave characteristics of the target material can be generated by the invention by use of a dielectric profiler which measures the amount of energy absorbed by the target material as a microwave frequency is swept across a microwave spectrum (the "profiling event"). Variations in the harmonics and the ratio between the fundamental wave frequency and harmonics are detected and assessed to generate a target material irradiation profile. The material irradiation profile can be used to control microwave characteristics applied to the target material to achieve a level of microwave absorption over a duration of time (the "irradiation event"). A first material irradiation profile of a material can be stored in a memory element and compared against a second material irradiation profile of the material to assess alteration of the material due to the irradiation event.

A computer (22) and associated software provides logistical and safety control of the various components or element of the invention. An interface (23) provides manual control(s), input control(s) and output control(s). A target material conveyer (1) can transport the target material (2) along the travel path of the invention. The target material (2) may be moved back and forth along the travel path by reversing the target material conveyer (1). The target material (2) can be located between at least one matrix array panel (26, 29) for the profiling event and a second matrix array panel (19, 20) for the irradiation event. The number of matrix panels utilized for the profiling event or the irradiation event, or both, may be tailored to suit the particular application.

A microwave generator (17) (variable frequency or otherwise) and a series of multiplexors (12, 14, 18, 21, 25, 30) can be connected to corresponding oscillators (15, 31) and detectors (11, 24) to provide a focused matrix array panel. Each element of the matrix array panel pair (26, 29 or 19, 20) can be connected to the corresponding multiplexor (12, 14, 18, 21, 25, and 30) by a network of microwave transmission lines or circuits (13). Infrared sensors, humidity sensors, or other sensors (21) can be coupled to the matrix array panel (20) to provide feedback on temperature rise. A safety module (16) provides protection against overloads.

The dielectric profiler can comprise a radiofrequency source (15 or 31) and a corresponding opposed radiofrequency detector (11 or 24) which can be calibrated over a wide frequency range. The calibration procedure encompasses each cell of a transmission element (19 or 29) and each corresponding cell of a receiver element (20 or 26) of the each matrix array panel used to during the profiling event associated with the target material (2). The component parts above-described, define the "radiofrequency network" of the invention.

Calibration of the radiofrequency network comprises the steps of using the computer (22) to locate the transmission element(s) (19 or 29) and the corresponding receiver elements (20 or 26) a distance apart according to an operators input (if the system is set for manual mode) or from sensors (32) if the system is in automatic mode. The target material (2) used for calibration can be located between the transmission element-receiver element pairs. The transmission element-receiver element pairs as shown by FIGS. 1, 2, 3 can be vertically oriented but as to certain embodiments of the invention the transmission element-receiver element pairs can be oriented horizontally or at other angles depending on the application. It is also possible for two transmission element-receiver element pairs to be mounted to form a square, or other geometric configuration, for use in processing all the surfaces of a target material (2) in one operation.

The computer (22) can adjust the oscillator of each radiofrequency source ("RF source") (15, 31) to a first frequency "x" and connects the output of the RF source (15, 31) through the selector (18, 30) to the matrix array panel (19, 29) to transmit cell "A". The output of the receiver cell "Ar" opposing the transmit cell "A" can be connected through the selector (12, 25) to the radiofrequency detector "RF detector" (11, 24). The analog output of the receiving cell "Ar" is proportional to the intensity of the radiofrequency field received from the transmit cell "A". The analog signal of receiver cell 'Ar" can be converted into a digital signal retrievably storable in a memory element of the computer (22).

The computer as to transmission cell "A" and receiver cell "Ar" can adjust the oscillator of each RF source (15, 31) to a second frequency "y" and the sequence of steps above-described can be repeated. Once a plurality of frequencies in the frequency range have been applied to the target material calibrated for the transmission cell "A" and receiver cell "Ar", as above-described, the computer calibrates a second transmission cell-receiver cell pair by the above-described steps. The steps in the sequence are repeated until all the transmission cell-receiver cell pairs in the matrix array panel (19, 20 or 29, 26) are calibrated.

Each transmission cell or receiver cell within a matrix array panel pair may itself be comprised of a number of "elements" to allow for a wide variety of target material configurations whether size or shape variations. Each element can undergo a similar sequence of calibration cycles.

Upon completion of the calibration procedure the computer (22) now has a "map" of the field intensity related the plurality of transmission cell-receiver cell pairs or plurality of element pairs within the matrix array panel or portion thereof utilized in the calibration event. The result of the calibration event is that substantially all of the radio frequency variables are "calibrated out" of the response of the radiofrequency network over the calibration frequency range. When a target material (2) is located between the cell pairs or element pairs of a calibrated matrix array panel pair (29, 26 or 19, 20), the signal from the corresponding detector (11 or 24) reflects the alteration of the microwave energy absorbed due to the dielectric characteristics of the target material (2) to which the dielectric profiling event was applied.

As the target material (2) is subjected to a dielectric profiling event, changes within the target material (2) can affect the relative amplitude of the harmonics of the fundamental frequency. Some harmonics may increase while others may decrease. These alterations in harmonics of the fundamental frequency form part of the dielectric profiling data gathered along with other dielectric profiling data such as exposure time, temperature, field intensity, or the like. The dielectric profiling data can be stored in the memory element of the computer (22) and can be used to generate a dielectric profile of the target material (2) which can be utilized to identify the target material (2) by comparison to dielectric profiles of target materials used as standards and can be further utilized as the basis for prescribing the microwave characteristics of the microwave irradiation event.

The dielectric profiling event for a target material (2) can be carried by repeating the steps of the calibration event above-described. Dielectric profiling event values can be mathematically manipulated to correct for all of the variables of the original calibration event. The results can be stored as the "dielectric profile" of the target material (2). The dielectric profile is a measure of the target material's absorption of the different frequencies within the microwave frequency spectrum applied during the dielectric profiling event. The frequency or frequencies that the target material absorbs most represents the frequency or frequencies to which the target material is most sensitive.

Once the dielectric profile for the target material (2) has been stored in the memory element of the computer (22) a map can be generated showing which frequency or frequencies are associated with energy absorption for that particular target material. As such, a plurality of dielectric profiles can be used as standard dielectric profiles to identify the corresponding target material in applications such as screening mail or baggage. The dielectric profile can also be used in conjunction with an application program to control the frequency and output power of a microwave generator (17) for subsequent microwave irradiation events.

If the target material (2) undergoes the microwave irradiation event utilizing the frequency and output power established by use of the dielectric profile in conjunction with the application program, alteration of the target material (2) due to the microwave irradiation event can be assessed by comparison of a first dielectric profile of the target material generated before the microwave irradiation event and second dielectric profile of the target material generated after the microwave irradiation event.

The computer (22) can be programmed to automatically select the appropriate field strength and duration of exposure(s) for any target material (2) identified by the dielectric profiler. Software may be used to manipulate the stored values to suit the particular application, for example it may be desirable to extend exposure time if a temperature or humidity change in the immediate environment surrounding the sample were to occur. In the embodiment of the invention shown by FIG. 1 there are two dielectric profilers; the first comprises elements 11, 12, 13, 33, 32, 14 and 15. The second comprises elements 24, 25, 26, 29, 30 and 31. The duplication of the dielectric profiler and the profiling event and the associated circuitry and computer application program can increase throughput and accuracy in an environment in which a large number discrete targets require assessment. It can avoid the need to reverse the target material conveyor (1) to re-appraise the target material (2) after the microwave irradiation event. The basic configuration of the embodiment of the invention shown by FIG. 1 may be repeated if increased speed, accuracy or throughput is required. The system could be a continuum of dielectric profiler 1, generator 1, dielectric profiler 2, generator 2, dielectric profiler 3 and so forth. The invention is normally operated under computer (22) control but a manual interface (23) is provided to allow local control of the invention if required.

Now referring primarily to FIGS. 2 and 3, a matrix of microwave antenna cells (7, 9) can be formed into a microwave transmission array (3) large enough to provide >100% coverage of the target material (2) to be examined or evaluated. Each transmission cell can be connected in turn to the microwave generator (17) through a multiplexer (14) (as shown by FIG. 1). The dwell time (the length of time each transmission cell stays connected to the microwave generator) is determined by the computer (22) which also controls the speed at which the target material (2) passes in front of the microwave transmission array (3).

Now referring specifically to FIG. 2, an embodiment of the microwave transmission array (3) can comprise a plurality of microwave antenna cells (7, 8 or 9) formed into a matrix (3, 4, 5, 6) which may be configured to optimize performance in the frequency bands of interest or accommodate the size and shape of the target material (2) to provide the optimum depth of field or provide a uniform intensity field, or both, for use in profiling events to detect and identify target materials. These attributes conserve power by focusing the energy; applying the optimum energy field strength over the desired area and minimizing collateral damage to surrounding objects or substances. There are many variations and permutations available in existing microwave antenna technology that can provide the desired matrix cell, aperture and gain. By combining numerous individual transmission elements (such as 10) with a parabolic reflector (7), or an alternative reflector (9) of less focal capability but perhaps wider bandwidth, an array with the desired beam width, bandwidth and gain may be produced.

The microwave energy (to or from) the individual cells within the overall matrix may be electronically manipulated to provide a series of macro-cells which allows a lower or higher resolution to be achieved. For example the matrix shown in FIG. 3 can be comprised of 36 cells in a 6×6 format. Each cell may be used individually or the energy from 2×2 or 3×3 or 4×4 or 2×4, or the like, can be combined to produce a desired distribution of microwave energy. Any permutation is possible within the constraints of normal microwave engineering problems such as insertion loss, bandwidth, reduced signal to noise ratio and the like. The individual transmission elements (10) within a transmission cell can also be configured as antennas with specified beam width and directivity. Individual cells (7, 9) may be "nested' to form a compound structure designed to achieve a specified bandwidth or other desirable characteristic. High and low frequency cells may be interleaved to achieve a specified bandwidth or other desirable characteristic. A matrix may be composed of as many cells as is desired, a practical limit will be set automatically by physical constraints or microwave engineering limitations.

For analysis of a small target material (2) or for analyzing small amounts of a target material (2), an individual "duplex cell" (7 and 8) can be used. Typically, one half of the cell could have a concave surface (7), the other a convex surface (8). Regardless of the surface profile actually used, both parts of the cell must mate together accurately. Membranes or coatings of inert material can be used to electrically isolate the surfaces of the transmission cell from the target material (2). Conductive bands, strips or arrays of elements (such as, but not limited to, dipoles) of conductive material, may be configured into the cell structure to provide the desired energy distribution profile. The cells can be moved by actuating mechanisms, such as but not limited to motors or piezoelectric crystals. Cells may be brought into close proximity under computer or manual control. Cells may be mounted in a sealed chamber for security, safety or other considerations such as cryogenic temperature analysis etc. Cells, especially those used for dangerous substance analysis or where cross contamination is a concern could be designed and manufactured to be disposable. The matrix assemblies can be moved by actuating mechanisms, such as but not limited to motors, air pistons, hydraulic rams etc. Matched pairs of matrix assemblies may be brought into close proximity under computer or manual control. Matched pairs of matrix assemblies may be mounted in a sealed chamber for security, safety or other considerations such as cryogenic temperature analysis, or the like. A version of the matrix assembly can be designed and manufactured to be disposable. Cells or matrix assemblies may be fitted with an integrated tracking device for security purposes. Cells or matrix assemblies may be fitted with an auto destruct mechanism to protect against the contents being exposed. Cells or matrix assemblies may be fitted with a device which provides a magnetic field or other form of desirable feature. Duplex cell pairs or matrix assemblies, which are pre-profiled may be made available for use by organizations requiring the ability to insert their substance, seal the matrix or duplex cell and send it to a third party (such as a government agency for example) for evaluation or treatment. The dielectric profiler function may be constructed to make use of the high power array elements in an interleaved configuration with the dielectric profiler. It can allow for repeated profiling events to be followed by high energy microwave irradiation events for extremely accurate control. It can have the added benefit of avoiding the need to move the target material (2) during the profiling event or the microwave irradiation event, or both. The position of the matrix panels can be adjustable and they may be configured automatically, if desired, by computer control. As the relative position of the panel is altered so the computer reconfigures and compensates for any change in focal or target illumination requirements. The invention can also be scaled to accommodate very large structures such as shipping containers, trucks, or the like, which may be moved automatically through the invention, as described for smaller targets such as letters, boxes, or the like. In such cases, array scanning techniques, doppler shift measurement and pulsed operation would provide benefits for large scale structure analysis. By configuring matrix panels in a cubic configuration, a 3D image of a target(s) internal structure may be constructed from a series of measurements using a uniform field absorption profile. For large area targets, some form of measurement correction, such as using doppler shift, or the like, could be included. For biological substances or objects, pulsed operation and the ability to accurately focus the energy ensures maximum control and minimal damage to surrounding substances.

As can be easily understood from the foregoing, the basic concepts of the present invention may be embodied in a variety of ways. The invention involves numerous and varied embodiments of a microwave sterilization system and methods of making and using such microwave sterilization system.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "profiler" should be understood to encompass disclosure of the act of "profiling"—whether explicitly discussed or not—and, conversely, were there effectively disclosure of the act of "profiling", such a disclosure should be understood to encompass disclosure of a "profiler" and even a "means for profiling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the microwave profiling or sterilization devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A method of irradiating a target material, comprising the steps of:
   a. performing a first profiling event of said target material;
   b. generating a first dielectric profile of said target material based on said first profiling event;
   c. generating a target material irradiation profile of said target material based on said first dielectric profile; and
   d. irradiating said target material with an amount of microwave radiation based on said target material irradiation profile.

2. A method of irradiating a target material as described in claim 1, further comprising the step of performing a second profiling event of said target material subsequent to irradiating said target material.

3. A method of irradiating a target material as described in claim 2, further comprising the step of generating a second dielectric profile of said target material based on said second profiling event.

4. A method of irradiating a target material as described in claim 3, further comprising the step of comparing said second dielectric profile said target material to said first dielectric profile of said target.

5. A method of irradiating a target material as described in claim 4, further comprising the step of assessing alteration of said target material based on comparison of said second target material irradiation profile to said first target material irradiation profile.

6. A method of irradiating a target material as described in claim 5, further comprising the step of establishing sufficiency of alteration of said target material based on comparison of said second target material irradiation profile to said first target material irradiation profile.

7. A method of irradiating a target material as described in claim 5, further comprising the steps of;
   a. establishing insufficiency of alternation of said target material based on comparison of said second target material irradiation profile to said first target material irradiation profile; and
   b. repeating said step of irradiating said target material with an amount of microwave radiation based on said target material irradiation profile to achieve said step of establishing sufficiency of alteration of said target material based on comparison of said second target material irradiation profile to said first target material irradiation profile.

8. A method of irradiating a target material as described in claim 1, wherein said step of performing said first profiling event comprises the steps of:
   a. generating a plurality of frequencies of microwave radiation which correspond to a swept microwave frequency spectrum;
   b. exposing said target material to said plurality of frequencies of microwave radiation which correspond to said swept microwave frequency spectrum; and
   c. detecting adsorption by said target material of each one of said plurality of frequencies of microwave radiation which correspond to said swept microwave frequency spectrum.

9. A method of irradiating a target material as described in claim 1, wherein said step of generating a first dielectric profile of said target material comprises the step of generating a measure of adsorption by said target material of each one of said plurality of frequencies of microwave radiation which correspond to said swept microwave frequency spectrum.

10. A method of irradiating a target material as described in claim 1, wherein said step of generating a target material irradiation profile of said target material based on said first profiling event comprises the step of identifying each one of said plurality of frequencies of microwave radiation which correspond to said swept microwave frequency spectrum absorbed by said target material.

11. A method of irradiating a target material as described in claim 10, wherein said step of generating a target material irradiation profile of said target material based on said first profiling event further comprises the step of establishing a power value of each one of said plurality of frequencies of microwave radiation which correspond to said swept microwave frequency spectrum identified as absorbed by said target material.

12. A method of irradiating a target material as described in claim 10, wherein said step of generating a target material irradiation profile of said target material based on said first profiling event further comprises establishing a duration value of each one of said plurality of frequencies of microwave radiation which correspond to said swept microwave frequency spectrum identified as absorbed by said target material.

13. A method of irradiating a target material as described in claim 1, wherein said step of irradiating said target material with an amount of microwave radiation based on said target material irradiation profile further comprises the step of:
   a. adjusting each one of said plurality of frequencies of microwave radiation which correspond to said swept microwave frequency spectrum identified as absorbed by said target material to;
   b. adjusting a duration of each one of said plurality of frequencies of microwave radiation which correspond to said swept microwave frequency spectrum identified as absorbed by said target material;
   c. irradiating said target material with at least one of said plurality of frequencies of microwave radiation which correspond to said swept microwave frequency spectrum identified as absorbed by said target material at said power and for said duration of time.

14. A method of irradiating a target material as described in claim 2, wherein said step of performing said second profiling event comprises the steps of:
   a. generating said plurality of frequencies of microwave radiation which correspond to a swept microwave frequency spectrum;
   b. exposing said target material to said plurality of frequencies of microwave radiation which correspond to said swept microwave frequency spectrum; and
   c. detecting adsorption by said target material of each one of said plurality of frequencies of microwave radiation which correspond to said swept microwave frequency spectrum.

15. A method of irradiating a target material as described in claim 3, wherein said step of generating a second dielectric profile of said target material comprises the step of generating said measure of adsorption by said target material of each one of said plurality of frequencies which correspond to said swept microwave frequency spectrum.

16. A method of identifying a target material, comprising the steps of:
a. performing a profiling event on each one of a plurality of standard materials;
b. generating a standard material dielectric profile corresponding to each one of said plurality of standard materials;
c. performing said profiling event on a target material;
d. generating a target material dielectric profile corresponding to said target material;
e. comparing said target material dielectric profile to said standard material dielectric profile generated for each one of said plurality of standard materials; and
f. matching said target material dielectric profile to said standard material dielectric profile of one of said plurality of standard materials to identify said target material.

17. A method of identifying a target material as described by claim 16, wherein said step of performing said profiling event comprises the steps of:
a. generating a plurality of frequencies of microwave radiation which correspond to a swept microwave frequency spectrum;
b. exposing said target material to said plurality of frequencies of microwave radiation which correspond to said swept microwave frequency spectrum; and
c. detecting adsorption by said target material of each one of said plurality of frequencies of microwave radiation which correspond to said swept microwave frequency spectrum.

18. A method of identifying a target material as described in claim 16, wherein said steps of generating a standard material dielectric profile corresponding to each one of said plurality of standard materials and of generating a target material dielectric profile corresponding to said target material comprise generating a measure of adsorption for each of said standard material and said target material of each one of a plurality of frequencies of microwave radiation which correspond to a swept microwave frequency spectrum.

19. A target material irradiator, comprising:
a. at least one microwave source which emits a plurality of frequencies of microwave radiation which correspond to a swept microwave frequency spectrum at a first power level in a first time duration;
b. a target material exposed to said plurality of frequencies of microwave radiation which correspond to said swept microwave frequency spectrum at said first power level in said first time duration;
c. at least one microwave detector which generates a signal which varies based on adsorption by said target material of each one of said plurality of frequencies of microwave radiation which correspond to said swept microwave frequency spectrum at said first power level in said first time duration;
d. a dielectric profiler which measures adsorption by said target material of each one of said plurality of frequencies which correspond to said swept microwave frequency spectrum at said first power level in said first time duration;
e. a target material irradiation profiler which identifies each one of said plurality of frequencies of microwave radiation which correspond to said swept microwave frequency spectrum absorbed by said target material at said first power level in said first time duration, and wherein said target irradiation profiler further establishes a power value of each one of said plurality of frequencies of microwave radiation which correspond to said swept microwave frequency spectrum identified as absorbed by said target material at said first power level in said first time duration, and wherein said target irradiation profiler further establishes a time duration value of each one of said plurality of frequencies of microwave radiation which correspond to said swept microwave frequency spectrum identified as absorbed by said target material a said first power in said first time duration; and
f. a microwave irradiator which irradiates said target material with at least one of said plurality of frequencies of microwave radiation which correspond to said swept microwave frequency spectrum identified as absorbed by said target material at said first power level in said first duration of time, wherein said microwave irradiator emits said at least one of said plurality of frequencies of microwave radiation at a second power level which corresponds to said established power value, and wherein said microwave irradiator emits said at least one of said plurality of frequencies of microwave radiation in a second time duration which corresponds to said established time duration value.

20. A target material irradiator as described in claim 19, where said at least one microwave source couples to a first one half of a duplex cell, and wherein said at least one microwave detector couples to a second one half of said duplex cell.

* * * * *